(12) United States Patent
Juneau

(10) Patent No.: US 7,370,394 B1
(45) Date of Patent: May 13, 2008

(54) SPIRITUAL STATUE SYSTEM

(76) Inventor: Virginia Irene Juneau, 6465 Hartman Rd., Lake Wales, FL (US) 33898

( * ) Notice: Subject to any disclaimer, the term of this patent is extended or adjusted under 35 U.S.C. 154(b) by 67 days.

(21) Appl. No.: 11/524,500

(22) Filed: Sep. 20, 2006

Related U.S. Application Data

(63) Continuation-in-part of application No. 10/642,820, filed on Sep. 17, 2004, now abandoned.

(51) Int. Cl.
*A61F 17/00* (2006.01)

(52) U.S. Cl. ............................................................. 27/1

(58) Field of Classification Search ...................... 27/1; D99/5, 19, 21; 446/73; 52/103
See application file for complete search history.

(56) References Cited

U.S. PATENT DOCUMENTS

| 232,782 | A | * | 9/1880 | Townsend ........................ 27/1 |
| 1,434,182 | A | * | 10/1922 | Zengen ........................ 52/103 |
| D312,058 | S |  | 11/1990 | Vermillion |
| 5,016,330 | A |  | 5/1991 | Botsch |
| D377,017 | S |  | 12/1996 | Giumarra |
| 6,023,822 | A |  | 2/2000 | Luebke |
| 6,200,507 | B1 |  | 3/2001 | Dennis |
| 6,439,946 | B1 | * | 8/2002 | Schneider ..................... 446/73 |
| 6,775,886 | B2 | * | 8/2004 | Ogle, II ............................. 27/1 |
| 6,785,938 | B1 | * | 9/2004 | Johansen, Jr. ..................... 27/1 |
| 7,043,803 | B2 | * | 5/2006 | Chen ................................ 27/1 |
| 2002/0100152 | A1 | * | 8/2002 | Ortega ............................ 27/1 |
| 2004/0040129 | A1 | * | 3/2004 | Ogle, II ........................... 27/1 |
| 2005/0120525 | A1 | * | 6/2005 | Heil et al. ......................... 27/1 |
| 2005/0125973 | A1 | * | 6/2005 | Hankel et al. .................... 27/1 |
| 2005/0166375 | A1 | * | 8/2005 | Cunningham et al. .......... 27/20 |

FOREIGN PATENT DOCUMENTS

CA 2255252 * 6/2000

* cited by examiner

Primary Examiner—William L. Miller
(74) Attorney, Agent, or Firm—Louis J. Brunoforte

(57) ABSTRACT

A statue has a front, a back, a head end above and a foot end below. A central section is between the head and foot ends. A recess is formed into the statue adjacent to the central section. A container is positioned in the recess and is adapted to receive mortal remains of a cremated being. The container has a front face. A stopper is positionable in an aperture of the container. A cover is secured in the recess and seals the recess with the container therein.

2 Claims, 3 Drawing Sheets

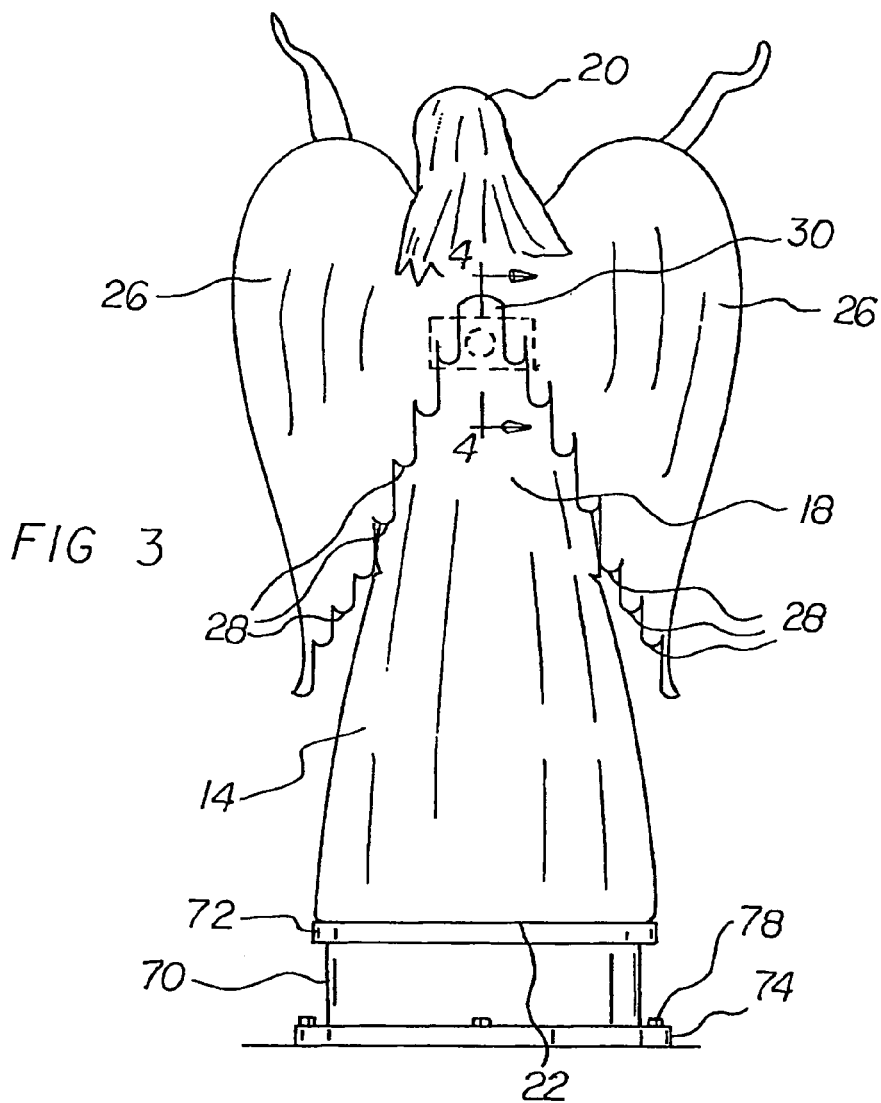
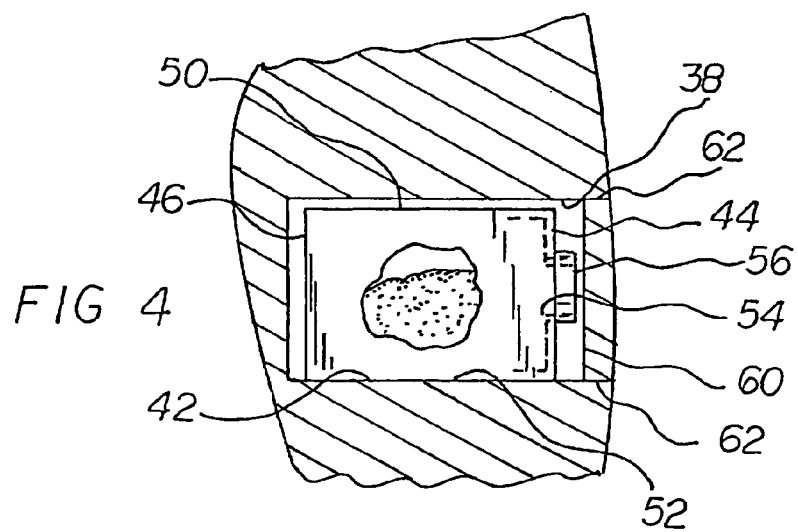
FIG 3
FIG 4

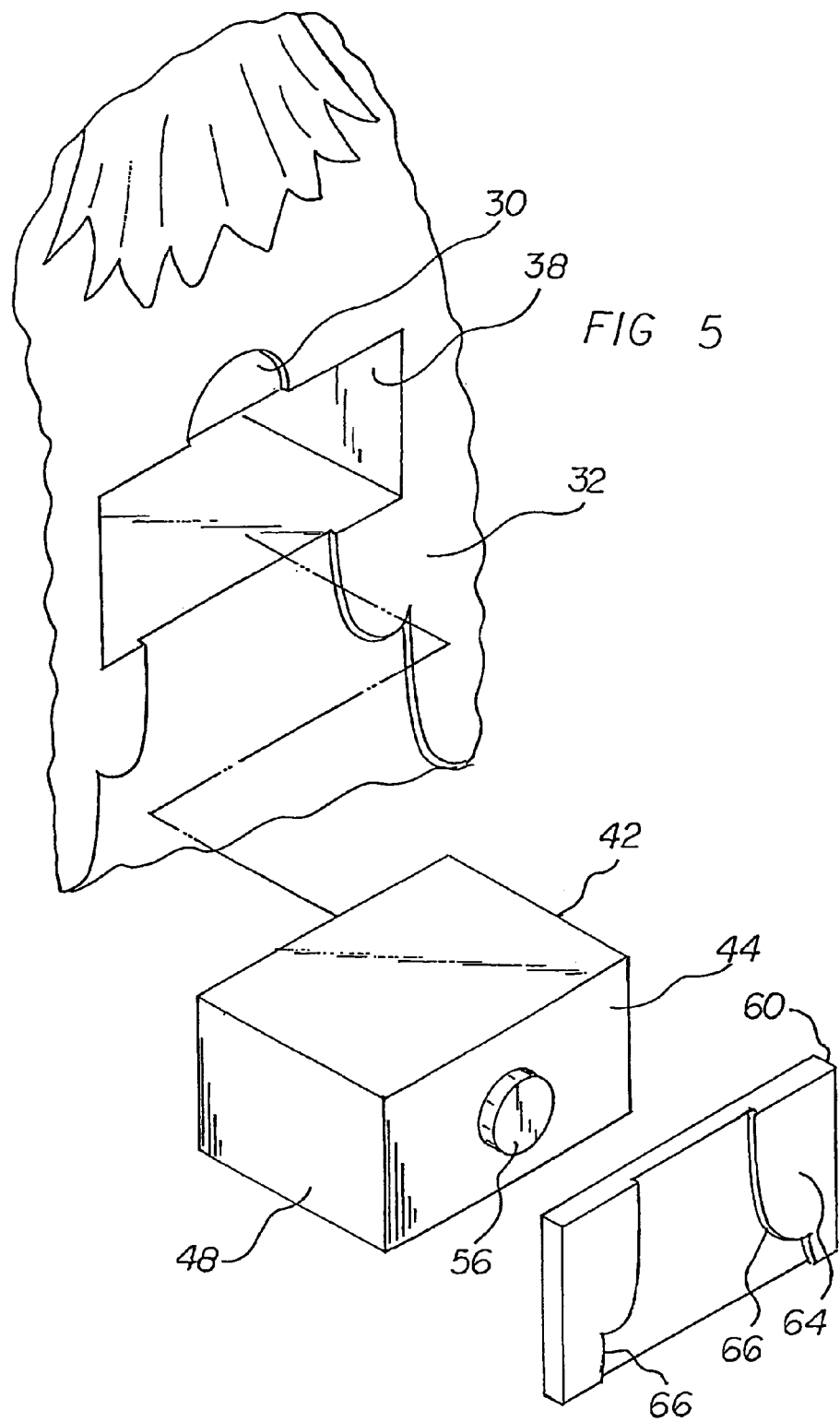

SPIRITUAL STATUE SYSTEM

RELATED APPLICATION

This application claims priority of and is a continuation-in-part of application Ser. No. 10/642,820 filed Sep. 17, 2004, now abandoned, entitled "Spiritual Statues" the subject matter of which is incorporated herein by reference.

BACKGROUND OF THE INVENTION

1. Field of the Invention

The present invention relates to a spiritual statue system and more particularly pertains to providing an appropriate final resting place for the mortal remains of a cremated person.

2. Description of the Prior Art

The use of urns of known designs and configurations is known in the prior art. More specifically, urns of known designs and configurations previously devised and utilized for the purpose of storing the mortal remains of cremated persons are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 6,023,822 issued Feb. 15, 2000 to Luebke relates to a Pet Crematory Urn. U.S. Pat. No. 5,016,330 issued May 21, 1991 to Botsch relates to a Personalized Pet Animal Memorial Product. U.S. Pat. No. 6,200,507 issued Mar. 13, 2001 to Dennis relates to a Method of Making a Memorial for Preservation of Remains of Deceased Individual. U.S. Pat. No. Des. 312,058 issued Nov. 13, 1990 to Vermillion relates to an Angel Figurine. Lastly, U.S. Pat. No. Des. 377,017 issued Dec. 31, 1996 to Giumarra relates to a Religious Statue Cassette Player.

While these devices fulfill their respective, particular objectives and requirements, the aforementioned patents do not describe a spiritual statue system that allows providing an appropriate final resting place for the mortal remains of a cremated person.

In this respect, the spiritual statue system according to the present invention substantially departs from the conventional concepts and designs of the prior art, and in doing so provides an apparatus primarily developed for the purpose of providing an appropriate final resting place for the mortal remains of a cremated person.

Therefore, it can be appreciated that there exists a continuing need for a new and improved spiritual statue system which can be used for providing an appropriate final resting place for the mortal remains of a cremated person. In this regard, the present invention substantially fulfills this need.

SUMMARY OF THE INVENTION

In view of the foregoing disadvantages inherent in the known types of urns of known designs and configurations now present in the prior art, the present invention provides an improved spiritual statue system. As such, the general purpose of the present invention, which will be described subsequently in greater detail, is to provide a new and improved spiritual statue system and method which has all the advantages of the prior art and none of the disadvantages.

To attain this, the present invention essentially comprises a spiritual statue system. First provided is a statue of a spiritual being. The statue has a front. The statue has a back. The statue also has a head end above. The statue further has a foot end below. A central section is provided between the head and foot ends. The statue also has wings. The wings extend laterally from the back of the statue more proximate the head end than the foot end. The wings are formed with a plurality of U-shaped designs. The designs have interior regions. The interior regions are formed into the back of the statue. The designs have exterior regions. The exterior regions are formed remote from the back. The statue has a height of about 5 feet. The statue has a maximum width of about 2 feet adjacent to the foot end. The statue has a minimum width of about 1 foot adjacent to the central section. The statue is preferably fabricated of concrete for an economical embodiment and bronze for an expensive embodiment.

A rectilinear recess is formed into the back of the statue adjacent to the central section. The recess has a width of about 11 inches. The recess has a height of about 8 inches. The recess has a depth of about 11 inches.

A hollow rectilinear container is provided. The container is positioned in the recess. The container is adapted to receive mortal remains of a cremated person. The container has a front face. The container has a parallel rear face. Parallel side faces are provided between the front and rear faces. The container has a top. The container has a parallel bottom coupling the faces above and below. The container has a width of about 10 inches. The container has a height of about 7 inches. The container has depth of about 9 inches. The front face has a circular aperture 54 for the passage of mortal remains of a cremated person. A cylindrical stopper is provided. The cylindrical stopper is positionable in the aperture. The container is fabricated of metal, preferably bronze, in the preferred embodiment.

Further provided is a rectilinear cover fabricated of concrete for an economical embodiment and bronze for an expensive embodiment. The cover has an adhesive, preferably mortar. The adhesive is secured in the recess and seals the recess with the container therein. The cover has an exposed face. The exposed face has laterally spaced curved indentations. The indentations are formed as extensions of the U-shaped designs of the wings.

Provided last is a pedestal. The pedestal is in a cylindrical configuration. The pedestal has an upper circular portion. The upper circular portion has a diameter greater than the pedestal. The upper circular portion receives the foot end of the statue. The pedestal has a lower circular portion. The lower circular portion has a diameter greater than the pedestal. In this manner a flange is formed. Apertures are provided through the flange. Bolts are provided. A horizontal recipient surface is provided. The bolts secure the pedestal and statue to the horizontal recipient surface. The pedestal has a plaque. The plaque has indicia. The indicia correspond to a cremated person whose remains are in the container. The plaque is located between the upper and lower circular portions beneath the front of the statue. The pedestal is preferably fabricated of concrete for an economical embodiment and bronze for an expensive embodiment.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved spiritual statue system which has all of the advantages of the prior art urns of known designs and configurations and none of the disadvantages.

It is another object of the present invention to provide a new and improved spiritual statue system which may be easily and efficiently manufactured and marketed.

It is further object of the present invention to provide a new and improved spiritual statue system which is of durable and reliable constructions.

An even further object of the present invention is to provide a new and improved spiritual statue system which is susceptible of a low cost of manufacture with regard to both materials and labor in an economical embodiment, and which accordingly is then susceptible of low prices of sale to the consuming public, thereby making such spiritual statue system economically available to the buying public.

Even still another object of the present invention is to provide a statue system for providing an appropriate final resting place for the mortal remains of a cremated being.

Lastly, it is an object of the present invention to provide a new and improved spiritual statue system. A statue has a front, a back, a head end above and a foot end below. A central section is provided between the head and foot ends. A recess is formed into the statue adjacent to the central section. A container is positioned in the recess. The container is adapted to receive mortal remains of a cremated being. The container has a front face. The container has an aperture. A stopper is positionable in the aperture. A cover is secured in the recess and seals the recess with the container therein.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated the preferred embodiment and alternate embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a rear elevational view of the system shown in FIGS. 1 and 2.

FIG. 4 is a cross sectional view taken along line 4-4 of FIG. 3.

FIG. 5 is an enlarged exploded view of the container and associated components as seen in FIGS. 3 and 4.

The same reference numerals refer to the same parts throughout the various Figures.

DESCRIPTION OF THE PREFERRED EMBODIMENT

Figure 1:
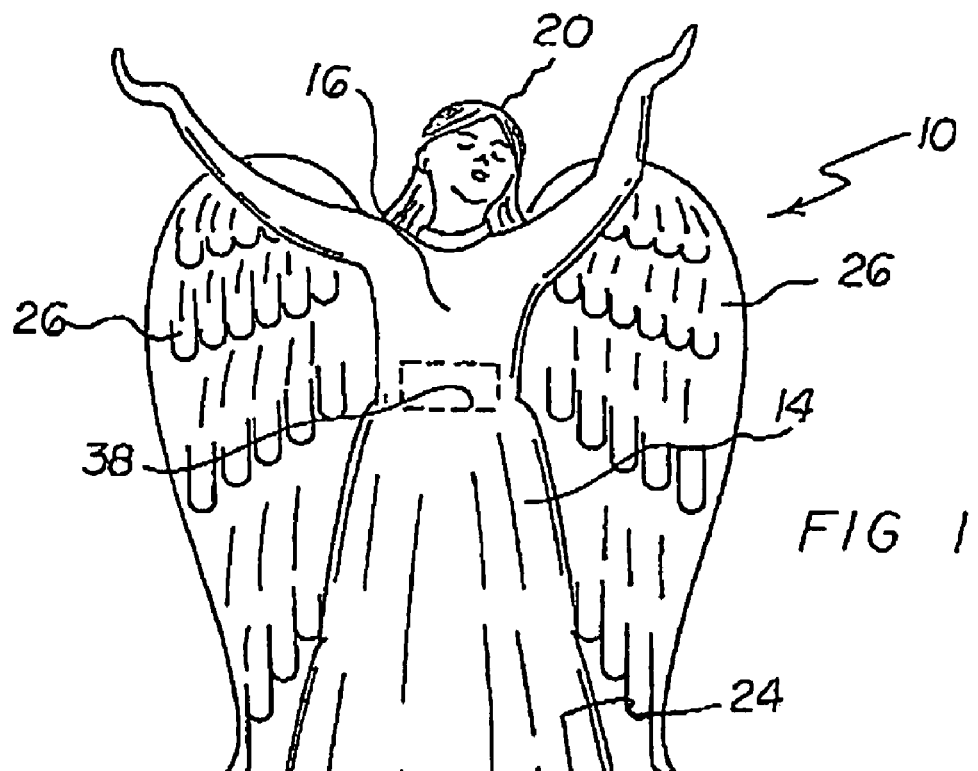
FIG. 1 is a front elevational view of a spiritual statue system constructed in accordance with the principles of the present invention.
Figure 2:
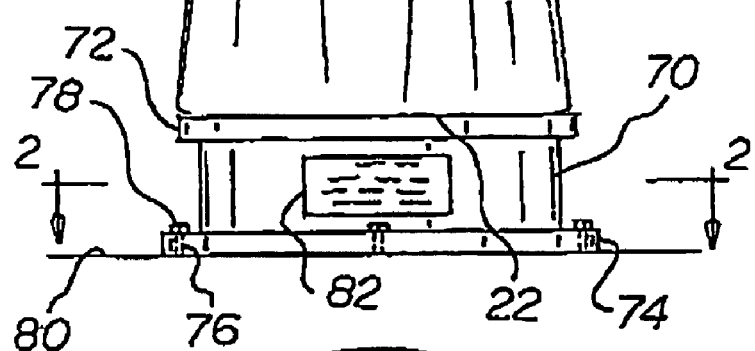
FIG. 2 is a cross sectional view taken along line 2-2 of FIG. 1.
Figure 2:
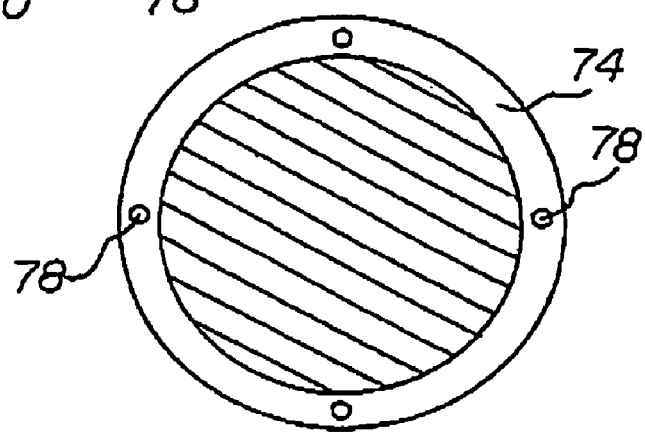

With reference now to the drawings, and in particular to FIG. 1 thereof, the preferred embodiment of the new and improved spiritual statue system embodying the principles and concepts of the present invention and generally designated by the reference numeral 10 will be described.

The present invention, the spiritual statue system 10 is comprised of a plurality of components. Such components in their broadest context include a statue, a recess, a container and a cover. Such components are individually configured and correlated with respect to each other so as to attain the desired objectives.

First provided is a statue 14, preferably of a spiritual being, an angel in the preferred embodiment. The statue has a front 16. The statue has a back 18. The statue also has a head end 20 above. The statue further has a foot end 22 below. A central section 24 is provided between the head and foot ends. The statue also has wings 26. The wings extend laterally from the back of the statue more proximate the head end than the foot end. The wings are formed with a plurality of U-shaped designs 28. The designs have interior regions 30. The interior regions are formed into the back of the statue. The designs have exterior regions 32. The exterior regions are formed remote from the back. The statue has a height of about 5 feet. The statue has a maximum width of about 2 feet adjacent to the foot end. The statue has a minimum width of about 1 foot adjacent to the central section. The statue is preferably fabricated of concrete for an economical embodiment and bronze for an expensive embodiment.

A recess 38, preferably of a rectilinear configuration, is formed into the back of the statue adjacent to the central section. The recess has a width of about 11 inches. The recess has a height of about 8 inches. The recess has a depth of about 11 inches.

A hollow rectilinear container 42 is next provided. The container is positioned in the recess. The container is adapted to receive mortal remains of a cremated person. The container has a front face 44. The container has a parallel rear face 46. Parallel side faces 48 are provided between the front and rear faces. The container has a top 50. The container has a parallel bottom 52 coupling the faces above and below. The container has a width of about 10 inches. The container has a height of about 7 inches. The container has depth of about 9 inches. The front face has a circular aperture 54 for the passage of mortal remains of a cremated person. A cylindrical stopper 56 is provided. The cylindrical stopper is positionable in the aperture. The container is fabricated of metal, preferably bronze, in the preferred embodiment.

Further provided is a rectilinear cover 60. The cover is fabricated of concrete for an economical embodiment and bronze for an expensive embodiment. The cover has an adhesive 62, preferably mortar. The adhesive is secured in the recess and seals the recess with the container therein. The cover has an exposed face 64. The exposed face has laterally spaced curved indentations 66. The indentations are formed as extensions of the U-shaped designs of the wings.

Provided last is a pedestal 70. The pedestal is in a cylindrical configuration. The pedestal has an upper circular portion 72. The upper circular portion has a diameter greater than the pedestal. The upper circular portion receives the foot end of the statue. The pedestal has a lower circular portion 74. The lower circular portion has a diameter greater than the pedestal. In this manner a flange is formed. Apertures 76 are provided through the flange. Bolts 78 are provided. A horizontal recipient surface 80 is provided. The bolts secure the pedestal and statue to the horizontal recipient surface. The pedestal has a plaque 82. The plaque has indicia. The indicia correspond to a cremated person whose remains are in the container. The plaque is located between the upper and lower circular portions beneath the front of the statue. The pedestal is fabricated of concrete for an economical embodiment and bronze for an expensive embodiment.

The present invention is disclosed in the primary as including a statue of a spiritual being such asn an angel to constitute the resting place for the remains of a human. The statute, cover and pedestal are fabricated of concrete for an economical embodiment and metal, preferably bronze, for an expensive embodiment. Other materials are adapted for us in other alternate embodiments. In addition, it should be understood that statues of other than spiritual beings are adapted for housing remains other than human remains, as for example cats and dogs and other pets. For pets, the statues, covers and pedestals of concrete are normally preferred.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A mortal remains statue system comprising:
    a statue having a front and a back with a head end above and a foot end below and with a central section between the head and foot ends;
    a recess formed into the statue adjacent to the central section;
    a container positioned in the recess adapted to receive the mortal remains of a cremated being, the container having a front face with an aperture and a stopper positionable in the aperture;
    a cover secured in the recess and sealing the recess with the container therein;
    a pedestal in a cylindrical configuration with an upper circular portion of a diameter greater than the pedestal receiving the foot end of the statue and a lower circular portion of a diameter greater than the pedestal to form a flange with apertures therethrough and bolts to secure the pedestal and statue to a horizontal recipient surface, the pedestal having a plaque with indicia corresponding to the cremated being whose remains are in the container, the plaque being located between the upper and lower circular portions beneath the front of the statue.

2. A mortal remains spiritual statue system for providing an appropriate final resting place for the mortal remains of a cremated person comprising, in combination:
    a statue of a spiritual being having a front and a back with a head end above and a foot end below and with a central section between the head and foot ends, the statue also having wings extending laterally from the back of the statue more proximate the head end than the foot end, the wings being formed with a plurality of U-shaped designs with the designs having interior regions formed into the back of the statue and exterior regions formed remote from the back, the statue having a height of about 5 feet and a maximum width of about 2 feet adjacent to the foot end and a minimum width of about 1 foot adjacent to the central section;
    a rectilinear recess formed into the back of the statue adjacent to the central section, the recess having a width of about 11 inches and a height of about 8 inches and a depth of about 11 inches;
    a hollow rectilinear container positioned in the recess adapted to receive the mortal remains of the cremated person, the container having a front face and a parallel rear face with parallel side faces between the front and rear faces and with a top and a parallel bottom coupling the faces above and below, the container having a width of about 10 inches and a height of about 7 inches and a depth of about 9 inches, the front face having a circular aperture for the passage of the mortal remains of the cremated person with a cylindrical stopper positionable in the aperture;
    a rectilinear cover with an adhesive secured in the recess and sealing the recess with the container therein, the cover having an exposed face with laterally spaced curved indentations formed as extensions of the U-shaped designs of the wings; and
    a pedestal in a cylindrical configuration with an upper circular portion of a diameter greater than the pedestal receiving the foot end of the statue and a lower circular portion of a diameter greater than the pedestal to form a flange with apertures therethrough and bolts to secure the pedestal and statue to a horizontal recipient surface, the pedestal having a plaque with indicia corresponding to the cremated person whose remains are in the container, the plaque located between the upper and lower circular portions beneath the front of the statue.

* * * * *